United States Patent [19]

Marugg et al.

[11] Patent Number: 4,939,182

[45] Date of Patent: Jul. 3, 1990

[54] MELAMINE-ALKANOLAMINE CONDENSATES AND POLYURETHANES PREPARED THEREFROM

[75] Inventors: John E. Marugg, Boerhaavelaan; Johan A. Thoen, Dommelstraat, both of Netherlands; Michael A. P. Gansow, Waedenswil, Switzerland

[73] Assignee: The Dow Chemical Company, Midland, Mich.

[21] Appl. No.: 225,311

[22] Filed: Jul. 27, 1988

[51] Int. Cl.$^5$ .............................................. C08L 61/00
[52] U.S. Cl. ................................... 521/136; 521/137; 521/138; 521/163; 521/188; 528/68; 528/76; 528/78; 528/85; 528/266
[58] Field of Search ............... 521/136, 137, 138, 163, 521/188; 528/68, 76, 78, 85, 266

[56] References Cited

U.S. PATENT DOCUMENTS

| | | | |
|---|---|---|---|
| 3,297,597 | 1/1967 | Edwards et al. | 521/166 |
| 4,356,304 | 10/1982 | Szita et al. | 544/196 |
| 4,367,294 | 1/1983 | Hahn et al. | 521/158 |
| 4,455,397 | 6/1984 | Reichel et al. | 521/166 |
| 4,485,195 | 11/1984 | Brennan et al. | 521/167 |
| 4,487,852 | 12/1984 | Brennan et al. | 521/167 |
| 4,489,178 | 12/1984 | Brennan et al. | 521/167 |
| 4,500,655 | 2/1985 | Brennan | 521/163 |
| 4,579,876 | 4/1986 | Iliopulos | 521/136 |
| 4,745,133 | 5/1988 | Grinbergs et al. | 521/128 |
| 4,774,268 | 9/1988 | Marx et al. | 523/179 |

Primary Examiner—John Kight, III
Assistant Examiner—Sam A. Acquah

[57] ABSTRACT

Condensates of certain amino-substituted s-triazines, formaldehyde and alkanolamines are disclosed. These condensates can be used, with or without alkoxylation, in forming polyurethanes having desirable burn properties.

22 Claims, No Drawings

MELAMINE-ALKANOLAMINE CONDENSATES AND POLYURETHANES PREPARED THEREFROM

BACKGROUND OF THE INVENTION

This invention relates to derivatives of melamine and other substituted melamine s-triazines, and to polyurethanes prepared therefrom.

Melamine and certain of its derivatives are known to be useful as flame retardant additives in polymeric materials, particularly in polyisocyanate-based polymeric foams. For example, the addition of melamine itself as a flame retardant additive is taught in U.S. Pat. No. 4,745,133, and GB Patent Nos. 2,177,405, 2,177,405 and 2,163,762. In addition, various derivatives of melamine, such as hydroxyalkylated melamines and melamine-formaldehyde resins, have also been incorporated into polyisocyanate-based polymers for various reasons, including imparting flame retardancy.

Unfortunately, the use of melamine and certain of its derivatives as additives increase the cost of the foam, and usually create problems in the processing or properties of the polymer, or both. This is a particular problem with melamine and its derivatives, as rather substantial amounts thereof are required to provide effective flame retardancy. Hydroxyalkylmelamine, for example, is high melting and is difficult to process in making polyurethanes. Melamine-formaldehyde resins are not stable, and tend to polymerize on standing. For such reasons, it is desired to reduce the level of flame retarding additives, instead preparing polymers using isocyanate-reactive materials which themselves impart flame retardant characteristics to the polymer. It would be especially desirable to provide an isocyanate-reactive material which can be reacted with a polyisocyanate to form a polymer having desirable physical properties and inherent flame retardant characteristics.

SUMMARY OF THE INVENTION

In one aspect, this invention is a condensate of an amino-substituted s-triazine, formaldehyde and at least one alkanolamine.

In another aspect, this invention is a polyol prepared by alkoxylating the condensate of this invention.

In another aspect, this invention is a polyisocyanate-based polymer which is prepared by reacting a polyisocyanate with the condensate or alkoxylated condensate of this invention.

The condensate and polyol of this invention can be reacted with a polyisocyanate to provide a polyisocyanate-based polymer having good flame retardant properties, as well as other desirable physical properties and processing characteristics. The condensate and polyol also are easily processed in preparing such polyisocyanate-based polymer.

DETAILED DESCRIPTION OF THE INVENTION

The condensation product of this invention is prepared in a condensation reaction of an amino-substituted s-triazine, formaldehyde and at least one alkanolamine.

The condensation reaction involves the condensation of an aldehyde, preferably formaldehyde, a primary or secondary amine and an amino-substituted triazine compound which contains at least one primary or secondary amine group. In this invention, the aromatic compound is a triazine compound having at least one amino group attached to a carbon atom in the triazine ring. Such triazine compounds include those represented by the structure

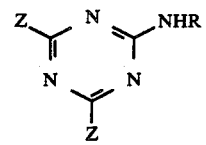

wherein each R is independently hydrogen, inertly substituted aryl or unsubstituted or inertly substituted alkyl and each Z is independently $NR_2$, hydrogen, or unsubstituted or inertly substituted alkyl. By inertly substituted, it is meant that the substituent group contains no moiety which undesirably interferes with the condensation reaction, an alkoxylation of the resulting condensate, or the reaction of the condensate or alkoxylated condensate with a polyisocyanate. Preferably, each R is independently hydrogen or $C_1-C_4$ alkyl, most preferably hydrogen. Each Z is preferably $NR_2$, $C_1-C_4$ alkyl, $C_1-C_4$ hydroxyalkyl, hydroxyl or hydrogen, and most preferably is $NH_2$. Exemplary compounds include melamine, ammelide, ammeline, guanamine, benzoguanamine and the like. Melamine is most preferred because it is readily available and provides excellent flame retardancy to an isocyanate-based polymer prepared from the condensate or the alkoxylated condensate.

The formaldehyde used is in any convenient form, with paraformaldehyde, trioxane, "inhibited" methanol solutions and the commonly available aqueous formalin solutions being exemplary. In commercial processes, the formaldehyde is preferably used as a concentrated aqueous solution, particularly as a 37% aqueous solution.

The ratio of substituted s-triazine formaldehyde and alkanolamine depends on the number of primary and secondary amino groups on the substituted s-triazine, as well as the desired functionality of the condensate. Since each primary or secondary amino group on the substituted s-triazine is a potential condensation site, up to three moles of formaldehyde can react per mole of substituted s-triazine. In this invention, a molar ratio of substituted s-triazine to formaldehyde of about 1:0.9 to about 1:3.5 is advantageously used. When the substituted s-triazine contains only one primary or secondary amino group, or it is desired to add only one (dialkanol)aminomethyl group to a more highly amino-substituted s-triazine, a ratio of closer to about 1:1 is preferred. Similarly, if an average of about two such groups are desired, a molar ratio of about 1:1.75 to about 1:2.5 is preferred. Likewise, a ratio of about 1:2.5 to about 1:3.5 is preferred when it is desired to add a average of more than two such groups. In this invention, it is preferred to add an average of about 1.5 to about 3, and more preferred to add an average of about 2 to about 3 (dialkanol)aminomethyl groups per molecule, and a molar ratio of substituted s-triazine to formaldehyde of about 1:1.75 to about 1:3.5 is most preferred.

The alkanolamine is either a monoalkanolamine, in which the nitrogen atom is mono- or disubstituted, or a dialkanolamine which is characterized by having two alkanol groups attached to a secondary nitrogen atom. The alkanol group on the monoalkanolamine is any which is unsubstituted or inertly substituted, with primary or secondary hydroxyl-substituted groups having about 2 to about 12, preferably 2 to about 6, more preferably about 2 to about 4 carbon atoms. The monoalkanolamine can also contain an inert substituent on the nitrogen atom, such as $C_1$–$C_{12}$, preferably $C_1$–$C_6$, alkyl and/or aryl substitution. Examples of such suitable monoalkanolamines are methylethanolamine, ethylethanolamine, methylisopropanolamine, ethylisopropanolamine, methyl-2-hydroxybutylamine, phenylethanolamine, ethanolamine, isopropanolamine and the like.

While monoalkanolamines can be used, they provide a lower functionality than do dialkanolamines, and their use is therefore less preferred. The preferred dialkanolamines advantageously contain primary or secondary hydroxyl-substituted alkyl groups having from about 2 to about 12, preferably about 2 to about 6, more preferably about 2 to about 4 carbon atoms. Exemplary dialkanolamines used herein include diethanolamine, diisopropanolamine, ethanolisopropanolamine, ethanol-2-hydroxybutylamine, isopropanol-2-hydroxybutylamine, isopropanol-2-hydroxyhexylamine, ethanol-2-hydroxyhexylamine, and the like. Of these, diethanolamine, diisopropanolamine and ethanolisopropanolamine are preferred. Mixtures of the foregoing dialkanolamines can also be used. Of particular interest are mixtures of diethanolamine and another alkanolamine, especially diisopropanolamine or ethanolisopropanolamine, as the use of these mixtures provides a condensate having a relatively low viscosity and a desirable reactivity.

The alkanolamine is normally employed in roughly equimolar quantities with the formaldehyde, such as at a ratio of about 1 mole of formaldehyde to about 0.75 to about 1.5 moles of alkanolamine.

In conducting the condensation reaction, the substituted s-triazine and the formaldehyde are advantageously contacted and permitted to react in a first step, followed by the addition of the alkanolamine. The formaldehyde is added to the substituted s-triazine at a rate which minimizes the exotherm. After the addition of the formaldehyde, it is generally useful to heat the mixture at an elevated temperature, such as about 30–100, preferably about 50–90, more preferably about 60°–80° C. in order to complete the reaction. A heating time of about 10 minutes to about 10 hours, preferably about 30 minutes to about 3 hours, is generally sufficient for this purpose. Completion of the reaction is sometimes indicated by the mixture becoming clear.

Following the formaldehyde addition, the alkanolamine is added and the resulting mixture is heated until the reaction is essentially complete. This can be determined by monitoring the water content of the mixture, as the condensation reaction produces water. As described below, in the usual processing, water is stripped from the reaction mixture as the reaction proceeds. As the reaction is completed, water is no longer produced, so when the water content becomes less than about 5% by weight, substantial completion of the reaction is indicated. The temperature is not especially critical, but is preferably below that temperature at which a substantial quantity of high molecular weight condensates are formed, and is sufficiently high on the other hand to provide an economically feasible reaction rate. Temperatures of about 40° to about 100° C. are preferred with about 50° to about 80° C. being more preferred, and 60° to about 75° C. being most preferred.

Following the completion of the condensation reaction, water is advantageously removed from the condensate. It is preferred to remove water under reduced pressure at a temperature of about 30 to about 100, preferably about 60 to about 100, more preferably about 80° to about 90° C. Water is advantageously removed until the condensate has a water content of less than about 5%, preferably less than about 1.5%, more preferably about 0.1 to about 1% by weight. Following removal of the water, it is preferred to further heat the condensate at about 50° to about 130° C., preferably about 100° to about 125° C. to further drive the reaction to completion.

It has been found that temperatures near the top of the ranges stated in the preceding paragraph, which are normally encountered near the end of the water removal step, tend to favor the formation of higher molecular weight polycondensates. This in turn causes the product to be a mixture of monomeric and higher molecular weight compounds. Unfortunately, in such cases the composition of the mixture tends to vary from batch to batch. Applicants have found, however, that the polycondensate forming reactions can be substantially reduced when the condensate is "capped" with a portion of the cyclic aliphatic ether prior to stripping the final portions of the water. This capping is preferably done by reacting the condensate with an alkylene oxide in the substantial absence of a basic catalyst prior to reducing the water content thereof to below about 0.5%, more preferably prior to reducing the water content to below about 1% by weight. The reaction of up to about 1 mole of alkylene oxide per dialkanolamine group on the condensate proceeds readily at moderate temperatures, and is very effective in reducing polycondensate formation during subsequent water removal and alkoxylation steps.

Although the resulting condensate is useful as a raw material in preparing polyurethanes, the condensate is preferably alkoxylated. Alkoxylation provides for a lower viscosity and therefore easier processing, and less brittleness in the resulting polymer. The alkoxylation is advantageously conducted to add an average of about 0.5 to about 25, preferably about 0.5 to about 5, more preferably about 0.75 to about 1.5 moles of alkylene oxide per hydroxyl group on the condensate, although it is recognized that the optimum amount of alkylene oxide addition will depend to a large extent on the end use of the product. In general, higher equivalent weight materials are useful in preparing flexible polyurethanes, whereas lower equivalent weight materials are useful in preparing rigid polyurethanes. As the polyols of this invention are especially useful in preparing rigid polyurethane foam, most preferably an average of about 1 to about 1.2 moles of alkylene oxide are added per hydroxyl group on the condensate.

The alkoxylation is advantageously conducted by reacting the hydroxyalkyl groups of the condensate with an alkylene oxide as is well known in the art.

The alkylene oxide used herein is any compound having an cyclic ether group and which is unsubstituted or inertly substituted, i.e., has no substituent groups which undesirably react with the condensate or which undesirably react under the conditions encountered in forming a polyurethane from the alkoxylated condensate. The cyclic ether group is preferably an α, β-oxirane, i.e., a three-membered cyclic ether ring. Preferred cyclic aliphatic ethers include those represented by the structure:

wherein each R is independently hydrogen or an unsubstituted or inertly substituted hydrocarbyl group, including unsubstituted or inertly substituted alkyl, aryl or arylalkyl groups. Exemplary inert substituent groups include acyclic ether, nitro, halogen, particularly chlorine or bromine, and like groups. Particularly preferred alkylene oxides include ethylene oxide, propylene oxide, 1,2- or 2,3-butylene oxide, the various isomers of hexane oxide, styrene oxide, epichlorohydrin, epoxycyclohexane, epoxycyclopentane, and the like. Most preferred, on the basis of performance, availability and cost, are ethylene oxide, propylene oxide, butylene oxide, and mixtures thereof, with ethylene oxide, propylene oxide or mixtures thereof being most especially preferred.

The manner by which the alkoxylation reaction is conducted is not especially critical to the invention. The cyclic aliphatic ether is advantageously added to the condensate at an elevated temperature, such as about 50 to about 180, preferably about 70 to about 160, more preferably about 90 to about 150° C. In the usual case where a volatile cyclic aliphatic ether is used, the reaction is preferably conducted under superatmospheric pressure, although superatmospheric pressure is not particularly beneficial when a non-volatile cyclic aliphatic ether is used. A catalyst can be used if necessary to provide a commercially viable reaction rate. Any catalyst which enhances the rate of polymerization of alkylene oxides is useful herein. Examples of such catalysts include basic compounds such as alkali metal hydroxides, alkali metal alkoxides, alkaline earth alkoxides, alkali metal and alkaline earth naphthenates, tertiary amine compounds, and the like, including those described, for example, in U.S. Pat. Nos. 3,393,243 and 4,595,743, incorporated herein by reference. Alkali metal hydroxides are generally preferred. Suitable processes for reacting a condensate with a cyclic aliphatic ether are disclosed, for example, in U.S. Pat. Nos. 3,297,597, 4,371,629, and 4,137,265.

Following the polymerization of the cyclic aliphatic ether, the resulting polyol is advantageously worked up by removing unreacted alkylene oxide, such as by vacuum stripping, and by removing or deactivating any residual catalyst, such as by neutralization with a weak acid and/or filtration.

The polyol of this invention is of particular interest in preparing polyurethanes of various types. Higher equivalent weight (800 or more, especially about 1000 to about 3000 equivalent weight) are useful in preparing elastomeric polyurethanes such as RIM elastomers, dynamic elastomers and flexible polyurethane foam. Polyols of this invention having an equivalent weight of about 800 or lower are useful, for example, as crosslinkers in elastomeric polyurethanes, and especially in making rigid polyurethane or polyurethane-polyisocyanurate foam. In making such polyurethanes, the polyol of this invention is reacted with a polyisocyanate, optionally in the presence of a blowing agent, other isocyanate-reactive compounds, surfactants and other auxiliaries useful in producing polyurethanes.

Polyisocyanates useful in making polyurethanes include aromatic, aliphatic and cycloaliphatic polyisocyanates and combinations thereof. Representative of these types are diisocyanates such as m- or p-phenylene diisocyanate, toluene-2,4-diisocyanate, toluene-2,6-diisocyanate, hexamethylene-1,6-diisocyanate, tetramethylene-1,4-diisocyanate, cyclohexane-1,4-diisocyanate, hexahydrotoluene diisocyanate (and isomers), naphthylene-1,5-diisocyanate, 1-methylphenyl-2,4-phenyldiisocyanate, diphenylmethane-4,4'-diisocyanate, diphenylmethane-2,4'- diisocyanate, 4,4'-biphenylenediisocyanate, 3,3'-dimethoxy-4,4'-biphenylenediisocyanate and 3,3'-dimethyldiphenylpropane-4,4'- diisocyanate; triisocyanates such as toluene-2,4,6-triisocyanate and polyisocyanates such as 4,4'-dimethyldiphenylmethane-2,2',5,5'-tetraisocyanate and the diverse polymethylenepolyphenylpolyisocyanates.

A crude polyisocyanate may also be used in making polyurethanes, such as the crude toluene diisocyanate obtained by the phosgenation of a mixture of toluene diamines or the crude diphenylmethane diisocyanate obtained by the phosgenation of crude diphenylmethanediamine. The preferred undistilled or crude polyisocyanates are disclosed in U.S. Pat. No. 3,215,652, incorporated by reference.

Especially preferred for making rigid polyurethanes are methylene-bridged polyphenylpolyisocyanates, due to their ability to crosslink the polyurethane. The isocyanate index (ratio of equivalents of isocyanates to equivalents of active hydrogen-containing groups) is advantageously from about 0.9 to about 10, preferably about 1.0 to about 4.0, more preferably about 1.0 to about 1.5.

In addition to the polyol and the polyisocyanate, various other components are useful in preparing polyurethanes. An additional isocyanate-reactive material, i.e., one which is not a polyol of this invention, may be employed in conjunction with the polyol of this invention. When an additional isocyanate-reactive material is used, sufficient of the condensate or polyol of this invention is present to provide a measurable improvement in flame retardancy in the resulting foam. Preferably, the condensate or polyol of this invention constitutes at least about 5, more preferably at least about 10, most preferably at least about 20 weight percent of the combined weight of the condensate or polyol and the additional isocyanate-reactive material, if any. When very high proportions of the condensate or polyol of this invention is present to the high viscosity and high reactivity sometimes make processing difficult. For that reason, such condensate or polyol preferably constitutes up to about 90, more preferably up to about 70, most preferably up to about 50 weight percent of the combined weight of the condensate or polyol of this invention and additional isocyanate-reactive material.

Suitable additional isocyanate-reactive materials for preparing rigid polyurethanes include those having an equivalent weight of about 50 to about 700, preferably about 70 to about 300 and more preferably about 70–150. Such additional isocyanate-reactive materials also advantageously have a functionality of at least 2, preferably about 3 to about 8 active hydrogen atoms per molecule.

Suitable additional isocyanate-reactive materials include polyether polyols, polyester polyols, polyhydroxy-terminated acetal resins, hydroxyl-terminated amines and polyamines, and the like. Examples of these and other suitable isocyanate-reactive materials are described more fully in U.S. Pat. No. 4,394,491, particularly in columns 3–5 thereof. Most preferred for preparing rigid foams, on the basis of performance, availability and cost, is a polyether polyol prepared by adding an alkylene oxide to an initiator having from about 2 to about 8, preferably about 3 to about 8 active hydrogen atoms. Exemplary such polyols include those commercially available under the trade names VORANOL* 250–473 polyol, VORANOL 240–360 polyol, VORANOL 270–370 polyol, VORANOL 240–446 polyol, VORANOL 240–490 polyol, VORANOL 575 polyol, VORANOL 240–800 polyol, all sold by The Dow Chemical Company, and PLURACOL**824 polyol, sold by BASF Wyandotte. Particularly useful additional isocyanate-reactive materials include alkoxylated Mannich condensates of a phenolic compound and an alkanolamine, as described in U.S. Pat. Nos. 3,297,597, 4,137,265 and 4,383,102, and aminoalkylpiperazine-initiated polyols as described in U.S. Pat. Nos. 4,704,410 and 4,704,411.

*Trademark of The Dow Chemical Company, **Trademark of BASF Corporation.

In making the preferred rigid foam, a blowing agent is suitably employed to impart a cellular structure to the foam. Useful blowing agents include those materials which generate a gas under the conditions of the polymerization of the reaction mixture Exemplary such materials include water, which reacts with isocyanate groups to liberate carbon dioxide, low boiling halogenated hydrocarbons such as fluorocarbons and fluorochlorocarbons, finely divided solids such as pecan flour, the so-called "azo" blowing agents which liberate nitrogen, and the like. Preferred blowing agents include water and the low boiling halogenated hydrocarbons. Water is particularly preferred in appliance and similar formulations, as it improves the flow properties of the formulation. When the polyurethane foam is desired to have thermal insulative characteristics, the blowing agent preferably comprises a low boiling halogenated hydrocarbon. Such blowing agents remain in the cells of the foam and contribute to the insulating properties thereof. Exemplary low boiling halogenated hydrocarbons include methylene chloride, tetrafluoromethane, trifluorochloromethane, dichlorodifluoromethane, CFC-142B, CFC-123, CFC-141B (all isomers) and the like.

Other auxiliaries useful in producing polyurethanes include surfactants, pigments, colorants, fillers, fibers, antioxidants, catalysts, flame retardants, stabilizers and the like. In making polyurethane foam, it is generally highly preferred to employ a minor amount of a surfactant to stabilize the foaming reaction mixture until it cures. Such surfactants advantageously comprise a liquid or solid organosilicone surfactant. Other, less preferred surfactants include polyethylene glycol ethers of long chain alcohols, tertiary amine or alkanolamine salts of long chain alkyl acid sulfate esters, alkyl sulfonic esters and alkyl arylsulfonic acids. Such surfactants are employed in amounts sufficient to stabilize the foaming reaction mixture against collapse and the formation of large, uneven cells. Typically, about 0.2 to about 5 parts of the surfactant per 100 parts by weight polyol are sufficient for this purpose.

One or more catalysts for the reaction of the polyol (and water, if present) with the polyisocyanate are advantageously used. Any suitable urethane catalyst may be used, including tertiary amine compounds and organometallic compounds. Exemplary tertiary amine compounds include triethylenediamine, n-methyl morpholine, pentamethyldiethylenetriamine, tetramethylethylenediamine, 1-methyl-4-dimethylaminoethylpiperazine, 3-methoxy-N-dimethylpropylamine, N-ethyl morpholine, diethylethanolamine, N-coco morpholine, N,N-dimethyl-N',N'-dimethyl isopropylpropylenediamine, N,N-diethyl-3- diethylaminopropylamine, dimethylbenzylamine and the like. Exemplary organometallic catalysts include organomercury, organolead, organoferric and organotin catalysts, with organotin catalysts being preferred among these. Suitable organotin catalysts include stannous chloride, tin salts of carboxylic acids such as dibutyltin di-2-ethyl hexanoate, as well as other organometallic compounds such as are disclosed in U.S. Pat. No. 2,846,408. A catalyst for the trimerization of polyisocyanates, such as an alkali metal alkoxide, may also optionally be employed herein. Such catalysts are used in an amount which measurably increases the rate of reaction of the polyisocyanate. Typical amounts are about 0.001 to about 1 parts of catalyst per 100 parts by weight of polyol.

In making a polyurethane foam, the polyol(s), polyisocyanate and other components are contacted, thoroughly mixed and permitted to expand and cure into a cellular polymer. The particular mixing apparatus is not critical, and various types of mixing head and spray apparati are conveniently used. It is often convenient, but not necessary, to pre-blend certain of the raw materials prior to reacting the polyisocyanate and active hydrogen-containing components. For example, it is often useful to blend the polyol(s), blowing agent, surfactants, catalysts and other components except for polyisocyanates, and then contact this mixture with the polyisocyanate. Alternatively, all components can be introduced individually to the mixing zone where the polyisocyanate and polyol(s) are contacted. It is also possible to pre-react all or a portion of the polyol(s) with the polyisocyanate to form a prepolymer, although such is not preferred in preparing rigid foam.

The polyurethane foam of this invention is useful in a wide range of applications, due to the desirable properties of the condensate or polyol and foam made therewith. Accordingly, not only can spray insulation be prepared, but appliance foam, rigid insulating boardstock, laminates, and many other types of rigid foam can easily be prepared with the condensate or polyol of this invention. Flexible foam is useful as, for example, cushioning materials in mattresses, furniture, automobile seating and the like.

The following examples are given to illustrate the invention and are not intended to limit the scope thereof. Unless stated otherwise, all parts and percentages are given by weight.

Example 1

The following general procedure is used to prepare melamine-formaldehyde-alkanolamine condensates in this and all subsequent examples.

In a suitable reactor are added 1 mole melamine and 3 moles formaldehyde (as a 37% solution in water). With continuous stirring, the mixture is heated to 70° C. After an hour at that temperature a clear mixture is obtained, indicating a complete reaction. At this time, analysis shows that the mixture has a pH of 8 and 13C—NMR shows that the —NH$_2$ groups of the melamine have been converted to a mixture of —NHCH$_2$OH (40–50%), —N(CH$_2$OH)$_2$, —NHCH$_2$OCH$_3$ and —N(CH$_2$OCH$_3$)$_2$ groups. To this mixture are added three moles of diethanolamine, and the resulting mixture is maintained at 75° C. with continuous stirring for an hour. The water is then removed under reduced pressure at about 75° C. until the water content of the product is reduced to about 2 to 5%. The resulting condensate has a viscosity of about 80,000 to about 100,000 cst at 25° C. and contains about 15 weight percent hydroxyl groups. It is referred to herein as melamine polyol A.

A portion of the resulting condensate is reacted with propylene oxide at a 1:6 molar ratio without catalyst at a temperature of 100°-110° C. and a slight positive nitrogen pressure. A total feed and digestion time of 20 hours is used. The resulting polyol has a viscosity of 35,000 cst at 25° C., an OH number of 541 and a basicity of 5.31 meq/g. It is referred to herein as melamine polyol B.

Example 2

Rigid polyurethane foam sample nos. 1-3 are prepared using melamine polyol A, using the formulations described in Table 1. Comparative Sample A is a control containing none of the melamine polyol.

TABLE 1

| | Parts by Weight | | | |
|---|---|---|---|---|
| Component | Comp. Sample A* | Sample No. 1 | Sample No. 2 | Sample No. 3 |
| Melamine polyol A | 0 | 20 | 40 | 50 |
| Supplemental polyol [1] | 90 | 70 | 50 | 40 |
| DMMP [2] | 10 | 10 | 10 | 10 |
| DMCHA [3] | 1 | 1 | 1 | 1 |
| Water | 1 | 1 | 1 | 1 |
| Silicone Surfactant [4] | 1 | 1 | 1 | 1 |
| Refrigerant 11 | 30 | 30 | 30 | 30 |
| Polymeric MDI, index [5] | 1.1 | 1.1 | 1.1 | 1.1 |
| Properties | | | | |
| Melamine Content [6] | 0 | 5 | 10 | 12.5 |
| Cream Time, sec | 46 | 24 | 13 | 21 |
| Gel Time, sec | 174 | 71 | 25 | 63 |
| Tack Free Time, sec | 240 | 91 | 40 | 77 |
| DIN 4102, cm [7] | 18 | 16 | 12.5 | 12 |

*Not an example of this invention.
[1] A tetrafunctional poly(propylene oxide) having a hydroxyl number of 490.
[2] dimethylmethylphosphonate
[3] dimethylcyclohexylamine
[4] B1049, sold by T. H. Goldschmidt
[5] A 2.7 functional polymeric MDI
[6] Weight melamine as a percentage of the weight of the polyol plus additives exclusive of polyisocyanate.
[7] Length of burn on a standard vertical burn test.

As can be seen from the data in Table 1, very substantial increases in reactivity are seen relative to the control. In addition, significant improvements in burn properties, as measured by a vertical burn test, are seen with this invention, even though an additional flame retardant is used, which tends to mask the impact of the polyol of this invention.

Example 3

Rigid polyurethane foam sample nos. 4-6 are prepared from melamine polyol B, using the formulations described in Table 2. Comparative Sample B is a control containing none of the melamine polyol.

TABLE 2

| | Parts by Weight | | | |
|---|---|---|---|---|
| Component | Comp. Sample B* | Sample No. 4 | Sample No. 5 | Sample No. 6 |
| Melamine polyol B | 0 | 10 | 20 | 30 |
| Supplemental polyol B [1] | 80 | 70 | 60 | 50 |
| Glycerine | 5 | 5 | 5 | 5 |
| TCEP [2] | 10 | 10 | 10 | 10 |
| DMCHA [3] | 1 | 1 | 1 | 1 |
| Water | 1 | 1 | 1 | 1 |
| Silicone Surfactant [4] | 1 | 1 | 1 | 1 |
| Trimerization Catalyst [5] | 0.5 | 0.5 | 0.5 | 0.5 |
| Refrigerant 11 | 40 | 40 | 40 | 40 |
| Polymeric MDI, index [6] | 1.4 | 1.4 | 1.4 | 1.4 |
| Properties | | | | |
| Melamine Content [7] | 0 | 1.5 | 3 | 4.5 |
| Cream Time, sec | 14 | 17 | 17 | 18 |
| Gel Time, sec | 32 | 36 | 37 | 37 |
| Tack Free Time, sec | 41 | 44 | 48 | 48 |
| DIN 4102, cm [8] | 14 | 12.5 | 12.5 | 12 |
| Free rise dens., kg/m3 | 24.3 | 25.6 | 25.8 | 25.8 |
| K-factor, mW/M-°K. | 18.1 | 16.0 | 16.2 | 16.2 |
| Compressive Str., KPa | | | | |
| ∥ to rise | 190 | 190 | 204 | 198 |
| ⊥ to rise | 89 | 81 | 83 | 72 |

*Not an example of this invention.
[1] The reaction product of 4 moles of propylene oxide per 1 mole of a condensate of nonylphenol, HCHO and diethanolamine at a 1:2:2 molar ratio.
[2] Trichloroethylphosphate.
[3] A Dimethylcyclohexylamine.
[4] B1049, sold by TH Goldschmidt.
[5] A 33% solution of potassium acetate.
[6] A 2.7 functional polymeric MDI.
[7] Weight melamine as a percentage of the weight of the polyol plus additives exclusive of polyisocyanate.
[8] Length of burn on a standard vertical burn test.

As can be seen from the data presented in Table 2, foams having very good properties are prepared using the alkoxylated melamine condensate of this invention. In particular, reactivity is only slightly reduced, even though the additional polyol used is a very reactive one, free rise density is not significantly changed, and there are significant improvements in both K-factor and flame retardance.

What is claimed is:

1. A condensate which is the reaction product of reactants consisting essentially of an amino-substituted s-triazine, about 0.9 to about 3.5 moles of formaldehyde per mole of amino-substituted s-triazine and about 0.75 to about 1.5 moles of at least one alkanolamine per mole of formaldehyde.

2. The condensate of claim 1 wherein said s-triazine is represented by the structure:

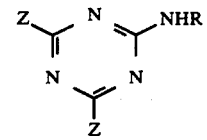

wherein each R is independently hydrogen, inertly substituted aryl or substituted or inertly substituted alkyl and each Z is independently NR₂, hydrogen, or unsubstituted or inertly substituted alkyl.

3. The condensate of claim 2 wherein said alkanolamine comprises a monoalkanolamine in which the nitrogen atom is mono- or disubstituted, or a dialkanolamine which is characterized by having two alkanol groups attached to a secondary nitrogen atom.

4. The condensate of claim 3 wherein each R is hydrogen or $C_1$-$C_4$ alkyl, each Z is $NR_2$ and the alkanolamine is diethanolamine or a mixture thereof with at least one other alkanolamine.

5. The condensate of claim 3 wherein the striazine is melamine, and the alkanolamine is diethanolamine or a mixture of diethanolamine and diisopropanolamine.

6. A polyol prepared by alkoxylating the condensate of claim 1.

7. A polyol prepared by alkoxylating the condensate of claim 5.

8. A hydroxyl-terminated compound containing a plurality of terminal hydroxylalkyl groups or terminal hydroxyl-terminated poly(oxyalkylene) groups attached to the residue, after removal of at least two hydroxyl hydrogen atoms, of a condensate which is the reaction product of reactants consisting essentially of an amino-substituted s-triazine, formaldehyde and at least one alkanolamine.

9. The compound of claim 8 which is the reaction product of ethylene oxide and/or propylene oxide with a condensation reaction product of melamine, formaldehyde and diethanolamine or a mixture thereof with another alkanolamine.

10. A polyether polyol initiated by a condensate which is the reaction product of reactants consisting essentially of an amino-substituted s-triazine, formaldehyde and an alkanolamine.

11. A polyisocyanate-based polymer which is prepared by reacting a reaction mixture comprising a polyisocyanate and the condensate of claim 1.

12. The polyisocyanate-based polymer of claim wherein said reaction mixture further comprises a blowing agent.

13. The polyisocyanate-based polymer of claim wherein said reaction mixture further comprises an additional polyol.

14. The polyisocyanate-based polymer of claim wherein said polyisocyanate comprises a polymethylenepolyphenylenepolyisocyanate.

15. The polyisocyanate-based polymer of claim which is a rigid polyurethane foam.

16. A polyisocyanate-based polymer which is prepared by reacting a reaction mixture comprising a polyisocyanate and the condensate of claim 5.

17. The polyisocyanate-based polymer of claim wherein said reaction mixture further comprises a blowing agent.

18. The polyisocyanate-based polymer of claim wherein said reaction mixture further comprises an additional polyol.

19. The polyisocyanate-based polymer of claim wherein said polyisocyanate comprises a polymethylenepolyphenylenepolyisocyanate.

20. The polyisocyanate-based polymer of claim 19 which is a rigid polyurethane foam.

21. A polyurethane foam prepared by reacting a reaction mixture comprising a polyisocyanate and the polyol of claim 6.

22. A polyurethane foam prepared by reacting a reaction mixture comprising a polyisocyanate and the polyol of claim 7.

* * * * *

UNITED STATES PATENT AND TRADEMARK OFFICE
CERTIFICATE OF CORRECTION

PATENT NO.  : 4,939,182

DATED       : July 3, 1990

INVENTOR(S) : John E. Marugg, Johan A. Thoen, and Michael A. P. Gansow

It is certified that error appears in the above-identified patent and that said Letters Patent is hereby corrected as shown below:

Column 10, line 66, claim 5, the word " striazine " should correctly read -- s-triazine --.

Column 11, line 27, claim 12, " polymer of claim " should correctly read -- polymer of claim 11 --.

Column 12, line 1, claim 13, " polymer of claim " should correctly read -- polymer of claim 12 --.

Column 12, line 4, claim 14, " polymer of claim " should correctly read -- polymer of claim 13 --.

Column 12, line 7, claim 15, " polymer of claim " should correctly read -- polymer of claim 14 --.

Column 12, line 12, claim 17, " polymer of claim " should correctly read -- polymer of claim 16 --.

Column 12, line 15, claim 18, " polymer of claim " should correctly read -- polymer of claim 17 --.

Column 12, line 18, claim 19, " polymer of claim " should correctly read -- polymer of claim 18 --.

Signed and Sealed this

Eighteenth Day of August, 1992

*Attest:*

DOUGLAS B. COMER

*Attesting Officer*       *Acting Commissioner of Patents and Trademarks*